US008926962B2

(12) United States Patent
Galiana et al.

(10) Patent No.: US 8,926,962 B2
(45) Date of Patent: Jan. 6, 2015

(54) TREATMENT OF PLANTS AGAINST OOMYCETE INFECTION

(75) Inventors: Eric Galiana, Antibes (FR); Michel Ponchet, Antibes (FR); Antoine Marais, Antibes (FR)

(73) Assignee: Institut National de la Recherche Agronomique (INRA), Paris (FR)

( * ) Notice: Subject to any disclaimer, the term of this patent is extended or adjusted under 35 U.S.C. 154(b) by 197 days.

(21) Appl. No.: 13/583,512

(22) PCT Filed: Mar. 11, 2011

(86) PCT No.: PCT/FR2011/000128

§ 371 (c)(1), (2), (4) Date: Dec. 5, 2012

(87) PCT Pub. No.: WO2011/110758

PCT Pub. Date: Sep. 15, 2011

(65) Prior Publication Data

US 2013/0071356 A1 Mar. 21, 2013

(30) Foreign Application Priority Data

Mar. 11, 2010 (FR) ..................................... 10 51767

(51) Int. Cl.
*A01N 63/04* (2006.01)

(52) U.S. Cl.
USPC .................................... 424/93.5; 435/195.15

(58) Field of Classification Search
USPC .................................... 424/93.5; 435/195.15
See application file for complete search history.

(56) References Cited

U.S. PATENT DOCUMENTS

| | | | | |
|---|---|---|---|---|
| 5,601,817 | A | 2/1997 | Sztejnberg et al. | |
| 6,544,512 | B1 | 4/2003 | White | |
| 2008/0022423 | A1 | 1/2008 | Roberts et al. | |
| 2010/0028303 | A1 | 2/2010 | Martin et al. | |
| 2011/0212541 | A1 * | 9/2011 | Tyler et al. | 436/501 |

FOREIGN PATENT DOCUMENTS

| | | |
|---|---|---|
| KR | 2003/0075092 | 9/2003 |
| WO | WO95/20879 | 8/1995 |
| WO | WO95/31106 | 11/1995 |
| WO | WO03/065811 | 8/2003 |
| WO | WO2010/009241 | 1/2010 |

OTHER PUBLICATIONS

Galiana E. et al. Ecosystem Screening Approach for Pathogen Associated Microorganisms Affecting Host Disease. Applied and Environmental Microbiology 77(17)6069-6075, Sep. 2011.*

Galiana E. et al. "*Phytophthora parasitica* biofilm formation: installation and organization of microcolonies on the surface of a host plant," Environmental Microbiology (Aug. 2008) vol. 10, No. 8, pp. 2164-2171.

Kaewchai S. et al. "Mycofungicides and fungal biofertilizers," Fungal Diversity (Sep. 2009) vol. 38, pp. 25-50.

EMBL Database, Jul. 5, 2012, "*Phoma* sp. Y3 EG-2010 18S ribosomal RNA gene, partical sequence," XPoo2648120, EBI accession No. EM_FUN:HM161743; Database accession No. HM161743.

International Search Report issued in PCT/FR2011/000128, dated Jul. 7, 2011.

* cited by examiner

*Primary Examiner* — Ralph Gitomer
(74) *Attorney, Agent, or Firm* — Lathrop & Gage LLP

(57) ABSTRACT

Treatment of plants against infection by oomycetes. The invention refers to a new strain of *Phoma* useful for manufacturing a plant-care composition intended to treat plants against phytopathogenic oomycetes. This new strain was deposited on Feb. 25, 2010 with the Collection Nationale de Cultures de Microorganismes of the Institut Pasteur in Paris, France under the CNCM number I-4278.

10 Claims, 2 Drawing Sheets

Constitution of a community of micro-organisms

Constitution of the biofilm

Figure 4

Identification of the isolates

Figure 1:
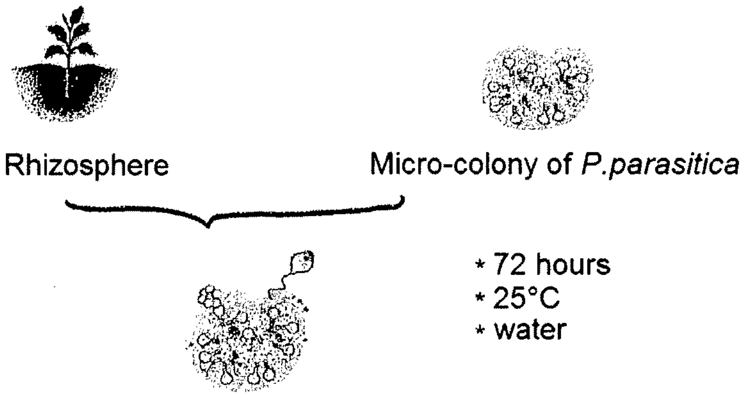

*In vivo* competition of isolates - *P. parasitica*

• Comparison with spores
• Comparison with mycelium

*In vivo* impact of the disease

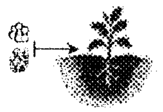

• Co-infection of the plant
• Pre-treatment

Figure 5A

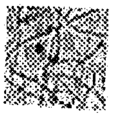

Figure 5B

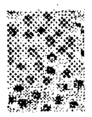

Figure 6

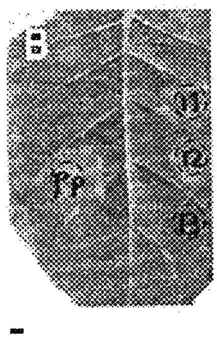

I1 : Extract of *P. parasitica* mixed with an isolate of penicilium
I2 : Extract of *P. parasitica* mixed with an isolate of *Aspergillus*
I1 : Extract of *P. parasitica* mixed with an isolate of a strain of *Phoma*
Pp : Extract of *P. parasitica* alone

Figure 7

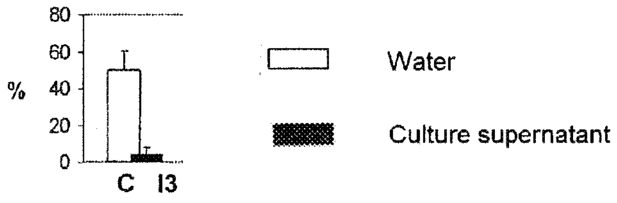

SEQUENCE LISTING

```
<160> NUMBER OF SEQ ID NOS: 3

<210> SEQ ID NO 1
<211> LENGTH: 1793
<212> TYPE: DNA
<213> ORGANISM: Phoma

<400> SEQUENCE: 1

ctggttgatc ctgccagtag tcatatgctt gtctcaaaga ttaagccatg catgtctaag      60

tataagcaat tataccgtga aactgcgaac ggctcattaa atcagttatc gtttatttga     120

tagtacctta ctacttggat aaccgtggta attctagagc taatacatgc taaaaacctc     180

gacttcggga ggggtgtatt tattagataa aaaaccaatg cccttcgggg ctctctggtg     240

attcataata acttctcaga tcgcatggcc ttgcgccggc gacggttcat tcaaatttct     300

gccctatcaa ctttcgatgg taaggtattg gcttaccatg gtttcaacgg gtaacgggga     360

attagggttc gattccggag agggagcctg agaaacggct accacatcca aggaaggcag     420

caggcgcgca aattacccaa tcccaatacg gggaggtagt gacaataaat actgatacag     480

ggctctttag ggtcttgtaa ttggaatgag tacaatttaa acctcttaac gaggaacaat     540

tggagggcaa gtctggtgcc agcagccgcg gtaattccag ctccaatagc gtatattaaa     600

gttgttgcag ttaaaaagct cgtagttgaa actttggcct ggctggcggg tccgcctcac     660

cgcgtgcatt cgcccggccg ggccttttct tctggagaac cgcatgccct tcactgggtg     720
```

-continued

```
tgttggggac caggactttt actttgaata aatcagagtg ttcaaagcag gcatttgctc    780

gaatacgtta gcatggaata atagaatagg acgtgcggtc ttattttgtt ggtttctaag    840

accgccgtaa tgattaatag ggacagtcgg gggcatcagt attcaattgt cagaggtgaa    900

attcttggat ttattgaaga ctaactactg cgaaagcatt tgccaaggat gttttcatta    960

atcagtgaac gaaagttagg ggatcgaaga cgatcagata ccgtcgtagt cttaaccata   1020

aactatgccg actagggatc gggcggtgtt actattttga ctcgctcggc accttacgag   1080

aaatcaaagt gtttgggttc tggggggagt atggtcgcaa ggctgaaact taaagaaatt   1140

gacggaaggg caccaccagg cgtggagcct gcggcttaat ttgactcaac acggggaaac   1200

tcaccaggtc cagatgaaat aaggattgac agattgagag ctctttcttg atttttcagg   1260

tggtggtgca tggccgttct tagttggtgg agtgatttgt ctgcttaatt gcgataacga   1320

acgagacctt aacctgctaa atagccaggc tagctttggc tggtcgccgg cttcttagag   1380

ggactatcgg ctcaagccga tggaagtttg aggcaataac aggtctgtga tgcccttaga   1440

tgttctgggc cgcacgcgcg ctacactgac agagccaacg agtttttttc cttggccgaa   1500

aggcctgggt aatcttgtta aactctgtcg tgctggggat agagcattgc aattattgct   1560

cttcaacgag gaatgcctag taagcgcgtg tcatcagcac gcgttgatta cgtccctgcc   1620

ctttgtacac accgcccgtc gctactaccg attgaatggc tcagtgaggc cttcggactg   1680

gctcgaggag gttggcaacg accaccctga gccggaaagt tcgtcaaact cggtcattta   1740

gaggaagtaa aagtcgtaac aaggtttccg taggtgaacc tgcagaagga tca           1793


<210> SEQ ID NO 2
<211> LENGTH: 17
<212> TYPE: DNA
<213> ORGANISM: Eucaryote

<400> SEQUENCE: 2

ctggttgatc ctgccag                                                     17


<210> SEQ ID NO 3
<211> LENGTH: 18
<212> TYPE: DNA
<213> ORGANISM: Eucaryote

<400> SEQUENCE: 3

tgatccttcy gcaggttc                                                    18
```

TREATMENT OF PLANTS AGAINST OOMYCETE INFECTION

CROSS-REFERENCE TO RELATED APPLICATIONS

This application is a U.S. National Stage application of international application PCT/FR2011/000128, filed in French on Mar. 11, 2011, which designates the United States, and which claims the benefit of FR1051767, filed in French on Mar. 11, 2010. Each of these applications is incorporated by reference herein in its entirety.

The invention relates to a micro-organism useful for the treatment of plants against infection by phytopathogenic oomycetes. The purpose of the invention is to use other sources of treatments than those usually used such as chemical or genetic treatments.

Oomycetes represent a phylum of filamentous protists comprising approximately 500 species. They are nonphotosynthetic aquatic organisms which, although looking like fungi, are far therefrom. Recent molecular studies made it possible to better classify them in the taxon of Stramenopiles. They are characterized by the existence, during their cycle, of a biflagellate cell.

Oomycetes live in water on organic wastes and carcasses of small animals. Certain species live in saprophytes in the soil on organic remains. Several species are very pathogenic for plants. Among phytopathogenic oomycetes, one knows the genus *Pythium* which includes many plant-parasitic species and some other animal-parasitic species. The genus *Phytophthora* is also responsible for diseases on wild and cultivated plants. *Plasmopara viticola* is the causal agent of grapevine mildew.

For example, the species *Phytophthora parasitica* (*P. parasitica*) causes a disease on plants, in particular on cultivated plants such as tomato, pepper, eggplant, citrus fruits, cocoa, tobacco. More precisely, the species *P. parasitica* is responsible for the occurrence of the “black shank” syndrome on tobacco.

The onset of the plant diseases due to infection by oomycetes is indicated by various symptoms observed on the leaves or roots (black foot rot, nanism, brown spots, then general withering of the leaves, a branch or all the plant). Oomycetes are frequently associated with the rhizosphere and can be transmitted through the soil.

Thus, many oomycetes are phytopathogenic micro-organisms, which is a serious problem for agriculture and environment in the world and causes considerable losses in the world (from 10 to 60% according to the plant cultivated) in particular due to *Phytophthora parasitica, sojae* and *ramorum, Plasmopara halstedii* and *viticola.*

In order to limit the impact of the diseases caused by oomycetes, fungicides are generally used, in particular metalaxyl, but also copper-based treatments, contact fungicides (maneb, mancozeb, fluazinam, . . . ) penetrating fungicides (cymoxanil), diffusing fungicides (dimetomorph, propamocarb) or systemic fungicides (oxadyxil). The number of active substances available is however reduced; moreover, not only there is a risk of oomycete resistance but these products can potentially be harmful for the environment.

Another alternative consists in creating disease-resistant plant varieties from a screening of the genetic resources available, according to conventional or biotechnological methods, as described for example in patent US2008 022423.

But, in the same way as for chemicals, oomycetes have the ability to get round varietal resistances; moreover, the development time for a resistant variety resulting from these genetic improvement programs proves to be rather long.

Treatments utilizing such micro-organisms as biological fight agents against various phytopathogenic fungi are also known; for example, patents WO95/20879, WO95/31106, WO03/065811, KR2003/0075092, WO2010/009241 teach the use of metabolites respectively produced by *Trichoderma*, of a *Fusarium* strain, of *Bacililus cereus* and *subtilis* strains, of a *Paenibacillus* strain, of a combination of *Trichoderma* and *Bacillus amyloliquefascians*, in order to fight in particular against *Phytophthora.*

However the professionals do not still have many methods for the biological control of oomycetes in spite of the renewed interest for these alternative methods. It is in this context that the inventors have looked for an alternative solution to chemical treatments that do not have the drawbacks of the other methods quoted above.

Thanks to a completely original method for identifying micro-organisms able to cohabit within a biofilm with at least one given species of phytopathogenic oomycete, the inventors have isolated a particular strain of micro-organism able to prevent an infection by said species of phytopathogenic oomycete from developing. More precisely, the inventors have discovered that this strain of micro-organism is able to control the growth of said phytopathogenic oomycete. The control of this growth is performed by inhibiting, at least partially, the growth of this phytopathogenic oomycete. The inventors were indeed interested in the microbial flora in the rhizosphere of a plant. On the surface of a host plant, the oomycete forms a biofilm other micro-organisms notably from the rhizosphere associate with. By biofilm one understands a film formed by a group of oomycetes, said oomycetes generating an adhesive protective matrix made up of polymeric substances and of so-called chemo-attractive substances which will attract the various micro-organisms from the rhizosphere.

The micro-organisms associated with biofilms have been selected in the course of time for their ability to cohabit with the phytopathogenic oomycete. Thus, the micro-organisms selected are probably those able to develop while using only the nutritive resource that are brought by the phytopathogenic oomycete; some of these micro-organisms are possibly able to inhibit, at least partially, the growth of the oomycete they are associated with.

When mixing the micro-organisms of the rhizosphere with the phytopathogenic oomycete, the inventors have isolated and characterized a new strain of micro-organism inhibiting the development of the oomycete.

In an embodiment example of the invention, the phytopathogenic oomycete is *Phytophthora parasitica* (*P. parasitica*). But it could be another species of phytopathogenic oomycete.

Thus, an object of the invention is a strain of filamentous fungus of the genus *Phoma* registered at the ‘Collection Nationale de Cultures de Microorganismes’ of the Pasteur Institute 25, Rue de Docteur Roux, F-75724 PARIS CEDEX 15 FRANCE, on Feb. 25, 2010 under the terms of the Budapest Treaty as CNCM number I-4278.

A molecular analysis enabled to establish that this strain comprised a ribosomal RNA 18S or rRNA 18S encoded by a gene of nucleotidic sequence SEQ ID N°1. This nucleotidic sequence SEQ ID N°1 is 98% identical to the nucleotidic sequence encoding rRNA 18S of *Phoma herbarum.*

The previously-identified strain of *Phoma* moreover shows the following features:

- it inhibits, at least partially, the growth of phytopathogenic oomycetes, it inhibits the growth of the oomycetes of the genus *Phytophthora,* it inhibits the growth of *Phytophthora parasitica.*

In the same embodiment example of the invention, the inventors have discovered that a culture supernatant of the strain of *Phoma*, object of the invention, inhibits the growth of *P. parasitica*. But it is understood that this supernatant could also inhibit, at least partially, the growth of other species of oomycetes.

Thus, an object of the invention is a culture supernatant of the previously-described strain, said culture supernatant inhibiting, at least partially, the growth of the phytopathogenic oomycetes.

Moreover, the invention presents the following features:

the supernatant comprises at least one metabolite having a size lower than or equal to a value between 0.18 μm and 0.22 μm, preferably lower than or equal to 0.2 μm.

the culture supernatant inhibits the growth of *Phytophthora parasitica.*

An object of the invention is also a method for obtaining the previously-mentioned supernatant, said method including the following steps of cultivating the previously-described strain, suspending the culture obtained, characterized in that it comprises the following step of filtering the suspension through a sieve having a diameter from 0.18 μm to 0.22 μm, preferably of 0.2 μm, collecting the filtered solution.

In a variant, before filtering the suspension, the method for obtaining makes provision for centrifuging the suspension between 1500 g and 6000 g for 1 to 10 minutes, preferably at 2000 g for 2 minutes.

An object of the invention is also another method for obtaining the previously-mentioned supernatant, including the following steps of cultivating the previously-described strain, suspending the culture obtained, characterized in that it comprises the following steps of centrifuging the suspension between 1500 g and 6000 g for 1 to 10 minutes, preferably at 2000 g for 2 minutes, then collecting the supernatant.

The previously-described strain can be used for manufacturing a plant-care composition intended to treat plants against infection by oomycetes. By plant-care composition, one understands a composition including, in addition to the strain of *Phoma* and/or a culture supernatant, as an active ingredient, agriculturally acceptable additives.

In the same nonrestrictive example of the invention, one of the species of oomycetes against which the strain is active is the species *P. parasitica*. But it could be another species of *Phytophthora* or another species of oomycete.

Thus, an object of the invention is also a plant-care composition, characterized in that it includes the previously-described strain of *Phoma.*

The culture supernatant of the registered and above-identified strain of *Phoma* can also be used for manufacturing a plant-care composition intended to treat plants against infection by phytopathogenic oomycetes.

Thus, an object of the invention is a plant-care composition, characterized in that it includes a culture supernatant as previously described.

In particular, the plants likely to be treated can be a plant of tobacco, tomato, potato, sweet pepper, grapevine, sunflower, fruit trees, or any other type of plant likely to be infected by the species phytopathogenic oomycetes.

An object of the invention is also a plant-care composition, characterized in that it includes the previously-described strain of *Phoma.*

An object of the invention is also a plant-care composition, characterized in that it includes a culture supernatant as previously described.

An object of the invention is also a plant-care composition, characterized in that it includes the previously-described strain of *Phoma* and the culture supernatant as previously described.

An object of the invention is also the use of the previously-described strain of *Phoma* for manufacturing a plant-care composition intended to treat plants against infection by phytopathogenic oomycetes.

An object of the invention is also the use of the previously-described culture supernatant for manufacturing a plant-care composition intended to treat plants against infection by phytopathogenic oomycetes.

Finally, an object of the invention is the use of the previously-described strain of *Phoma* and the previously-described culture supernatant for manufacturing a plant-care composition intended to treat plants against infection by phytopathogenic oomycetes.

The invention will be better understood when reading the following description and examining the annexed figures. These figures are given only as an indication and by no means a restriction of the invention. In Figures it is shown:

FIG. 1: a schematic representation of a formation of a group of micro-organisms from a rhizosphere of a plant and a micro-colony of *P. parasitica;*

Figure 2:
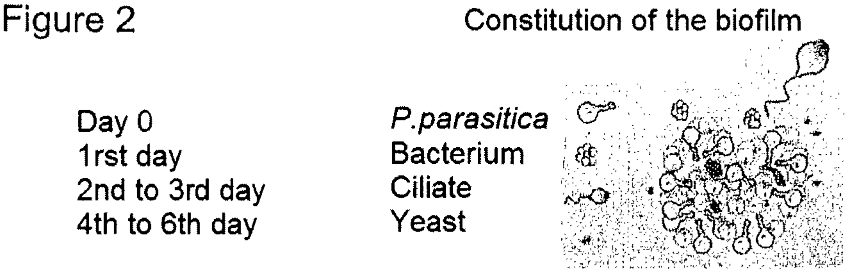

FIG. 2: a schematic representation of a formation of a biofilm from a colony of *P. parasitica;*

Figure 3:
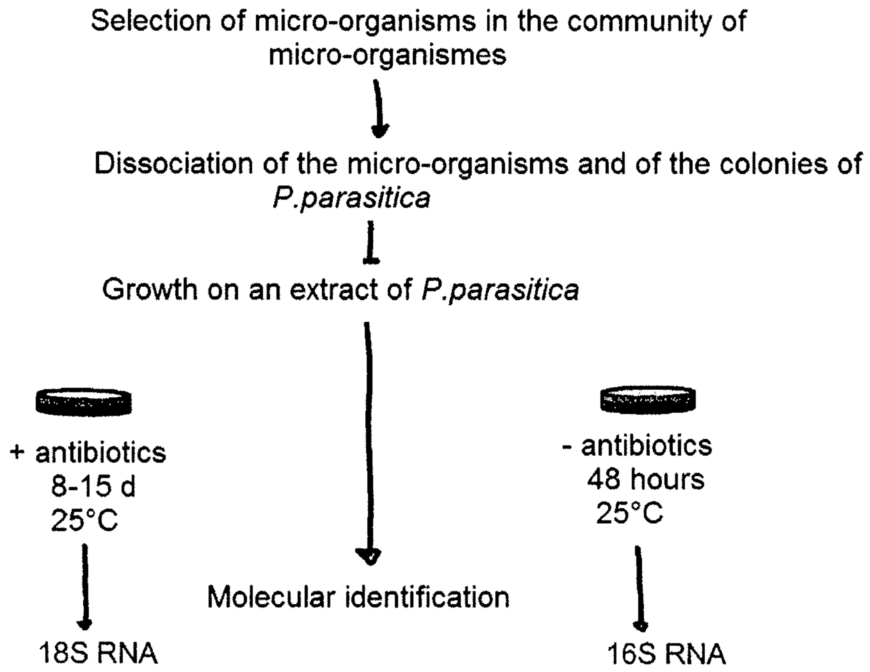

FIG. 3: a schematic representation of a method for selecting micro-organisms able to live in the presence of *P. parasitica;*

FIG. 4: schematic representations of an in vitro and in planta co-infection of *P. parasitica* and of micro-organisms able to live in the presence of *P. parasitica;*

FIG. 5A: an optical microscope photography of a culture medium including only one filtrate including water and the species *P. parasitica;*

FIG. 5B: an optical microscope photography of a culture medium including *P. parasitica* and a culture supernatant of micro-organisms from the isolate I3 selected for the ability of the same micro-organisms from the isolate I3 to survive in the presence of *P. parasitica;*

FIG. 6: a photography of a tobacco leaf which has been brought in contact with zoospores of *P. parasitica* only (Pp) or in contact with zoospores of *P. parasitica* mixed with spores from various micro-organisms (I1*: Penicillium*, I2*: Aspergillus* and I3: strain of *Phoma*), and FIG. 7: A graphic representation in percentage of the effect of a culture supernatant of micro-organisms on the germination of zoospores of *P. parasitica* (I3) and of the effect of another water-containing filtrate on the growth of *Phytophthora parasitica* (C), said micro-organisms coming from a I3 isolate selected for the ability of the micro-organisms contained in this isolate to survive in the presence of *P. parasitica.*

1—EQUIPMENTS AND METHODS

1.1. Constitution of the Community (FIG. 1)

A 5-week-old tobacco plant were brought under cultivation in a compost sold in the stores and cultivated at 24° C. in a plant laboratory, with a photoperiod of 16 hours and a luminous intensity of 100 $\mu Em^{-2}sec^{-1}$. After 5-week growth, samples of soils were taken from the rhizosphere of this plant. These samples were mixed with sterile water (1/5, W/V). The rhizospheric microbial flora (size of the micro-organisms <100 μm) were obtained by means of two successive filtrations through a sieve having a diameter of 100 μm. After a fast period of decantation, the supernatant (5 ml) obtained from the filtrate were incubated at 24° C. with micro-colonies of *Phytophthora parasitica* (or *P. parasitica*) prepared as described in E. Galiana, S. Fourré, G. Engler, *Environ. Microbiol.* 10, 2164-2171 (2008) and washed three times with water. The kinetics of the colonization of the micro-colonies of *P. parasitica* by rhizospheric micro-organisms were determined after observation under an optical microscope.

1.2. Selection of the Community (FIGS. 2 and 3)

The mixture of rhizospheric micro-organisms and of microcolonies of *P. parasitica* form a biofilm. After three-day incubation, the biofilms obtained were rinsed three times with water. The micro-organisms and the microphone-colonies of *P. parasitica* forming the biofilms were then smoothly dissociated from one another through the opening of a Pasteur pipette. The resulting suspension of micro-organism cells were incubated on an agar gel in a Petri dish. The agar gel contained an extract of *P. parasitica* as the sole source of nutrient (row extract of *P. parasitica* 10 g/L; NaCl 10 g/L; agar 1.5% (P/V)). The row extract of *P. parasitica* were prepared from a two-week-old mycelium from the strain 329 of *P. parasitica* (INRA, Sophia-Antipolis). The mycelium were washed with water, ground to a fine powder in a mortar and in liquid nitrogen, then subjected to freeze drying. In order to select the micro-organisms eukaryotes, the Petri dishes were supplemented with 30 μg/ml of chloramphenicol.

About thirty isolates were identified as micro-organisms eukaryotes forming the biofilm and able to grow on the medium thus prepared, among which the isolates designated I1, I2, I3 were subjected to an analysis which will be more detailed hereafter.

By isolate one understands at least one colony of micro-organisms able to grow on the medium prepared as described above, said micro-organisms being identical to each other.

1.3. Molecular Identification (FIG. 3)

For each isolate, a sample of micro-organism cells were taken and subjected to a molecular PCR analysis.

The sample were prepared by suspending cells, spores and the mycelia in boiling water for 3 minutes, and then chilled with ice and centrifuged at 10.000 g for 3 minutes in order to eliminate remains.

The supernatant (1 μL) were subjected to a PCR amplification of the DNA encoding the eukaryotic ribosomal RNA 18S by using the forward primer EukA or SEQ ID N°2: 5'-CTGGTTGATCCTGCCAG-3' and the reverse primer EukB or SEQ ID N°3: 5'-TGATCCTTCYGCAGGTTC-3' (G. Petroni, F. Dini, F. Varnished, G. Rosati, *Mol. Phylogenet. Evol.* 22, 118-130 (2002)).

The PCR program included an initial denaturation at 94° C. for 120 seconds, followed by 35 cycles of denaturation at 94° C. for 30 seconds, then a hybridization at 56° C. for 45 seconds and an extension at 72° C. for 120 seconds.

1.4. Identification of the Micro-Organisms Having an Impact on the Growth of *P. parasitica* and the Disease of the Plant. (FIGS. 4, 5A, 5B, 6, 7)

This identification were performed on the one hand in vitro (FIGS. 4, 5A, 5B, 7) by comparing the micro-organisms representative of each previously-obtained isolate with two strains of *P. parasitica*, and on the other hand also in planta (FIG. 4, 6) by means of co-infections.

For in vitro comparisons, the strains of *P. parasitica* and the micro-organisms representative of each previously-obtained isolate were brought under cultivation on agar V8. Then the mycelial discs obtained (5 mm of diameter) were transferred into a new Petri dish containing agar V8 and placed on the right part for *P. parasitica* and on the left part for the isolate. The inhibition area that can be seen around the disc of the isolate were used to measure the anti-*P. parasitica* activity.

The effect of the micro-organisms from each isolate I1, I2 and I3 on the germination of *P. parasitica* was also tested on microscope slides. A suspension of zoospores (10 μL) of *P. parasitica* (4.105 cells/ml) was mixed with an equal volume of medium V8 and water incubated beforehand with each isolate tested, then filtered. The water thus conditioned was prepared by incubating mycelial discs in sterile water (1 ml) for one hour at 25° C. After a centrifugation at 2000 g for 2 minutes, the supernatant was filtered through a filter having a porosity of 0.2 μm in order to eliminate the remains and the residual cell material. The centrifugation can also be performed at a value in a range of values from 1500 g to 6000 g and for 1 minute to 10 minutes. Preferably, the centrifugation was performed at 2000 g for 2 minutes.

The supernatant can be filtered or not filtered. It is generally filtered after centrifugation to get rid of the cellular remains which could be mixed with the supernatant at the time of its taking.

It is also possible no to centrifuge the suspension obtained after incubation of the mycelial discs in sterile water for 1 hour which is then directly filtered with the filter having a porosity of 0.2 μm.

The filter can have a porosity value which can also vary in a range of values from 0.18 μm to 0.22 μm, preferably the filter has a porosity of 0.2 μm.

FIGS. 5A and 5B illustrate an experiment performed with the micro-organism representative of the isolate I3.

The percentage of germination were determined after a two-hour incubation of the zoospores in the presence of the filtered supernatant from the isolate I3 at 25° C., FIG. 7.

Regarding the analysis and screening in planta (FIG. 6), the co-infection was performed in the parenchymatous tissue, a suspension of 100 μL containing 500 zoospores of *P. parasitica* and 500 spores of the micro-organism representative of each isolate was infiltrated into the right part of tobacco leaves being 4 to 6 weeks old. In particular, in FIG. 6 it is illustrated the effect of the micro-organism representative of each of the three isolates I1, I2, I3 on the leaf. The surfaces showing the symptoms typical of an invasion by *Phytophthora* were measured 2 days after co-inoculation. In order to evaluate the impact of the micro-organisms representative of each isolate on the progression of the infection, these surfaces were compared with those measured with the left part of the leaf that was inoculated with 500 zoospores of *P. parasitica* only. It should be noted that no micro-organism in each isolate caused the development of symptoms on the plant when these were inoculated without zoospores *P. parasitica* (for 7 days) or showed a phytotoxicity.

1.5. Identification of the rRNA 18S of the Micro-Organisms of Each Isolate I1, I2 and I3

1.5.1. PCR Amplification of rRNA 18S

The rRNA 18S of the micro-organisms corresponding to each isolate I1, I2 and I3 was amplified by the PCR technique. To this end, it was used, as previously described, a sense primer of the nucleotidic sequence SEQ ID N°2 and an anti-sense primer of the nucleotidic sequence SEQ ID N°3.

1.5.2. Identification of the Micro-Organisms

The amplification products corresponding to the rRNA 18S were cloned in the vector pGEMT-easy (Promega), sequenced and compared with the sequences already in the data banks using the program blastn (http://blast.ncbi.nlm.nih.gov.gate1.inist.fr/Blast.cgi?PROGRAM=blastn&BLAST_PROGRAMS=megaBlast&PAGE_TYPE=BlastSearch&SHOW_DEFAULTS=on&LINK_LOC=blasthome)

2—RESULTS

After analyzing the amplified nucleotidic sequences of rRNA 18S, the micro-organism in the isolate I1 was identified as a *Penicillium*. The micro-organism in the isolate I2 was *Aspergillus*. The micro-organism in the isolate I3 was *Phoma*.

FIG. 5B shows the absence of mycelial filaments produced by *P. parasitica* in the presence of the filtered culture supernatant of micro-organisms representative of the isolate I3. Thus, the inventors noted that the filtered culture supernatant resulting from the isolate I3 inhibited the growth of *P. parasitica.*

According to the aspect of the tobacco leaf obtained after co-infection (FIG. 6), the inventors also noted that, at the place where the spores of the isolates I1 and I2 mixed with *P. parasitica* and *P. parasitica* alone were inoculated, the symptoms of the disease caused by *P. parasitica* appeared. Only the place where the spores of the isolate I3 with *P. parasitica* were inoculated did not present these symptoms. By this experiment, the inventors confirmed that the micro-organism in the isolate I3 presented an inhibiting activity on the growth of *P. parasitica* in the plant.

Because of this inhibiting activity potentially interesting for the biological fight against the infection of the plants by *P. parasitica*, the micro-organism in the isolate was identified. A morphological study with a microscope showed that this micro-organism was a filamentous fungus whose spores presented a brown color. The nucleotidic sequence encoding the rRNA 18S of this micro-organism or SEQ ID N°1 is 98% identical to the sequence having a nucleotidic sequence encoding the rRNA 18S of the strain *Phoma herbarum.*

From the above-described results it follows that this new strain of *Phoma* in this isolate I3 and/or the culture supernatant of this strain can thus be used as a basis for the development of a plant-care composition in order to treat plants infected or likely to be infected by at least one phytopathogenic oomycete.

REFERENCES

J. W. Costerton, P. S. Stewart, E. P. Greenberg, *Science* 21, 1318-1322 (1999).
T. Danhorn, C. Fuqua, *Annu. rev. Microbiol.* (2007).
A. D. Kent, E. W. Triplett, *Annu. Rev. Microbiol.* 56, 211-236 (2002).
B. Stecher, W. D. Hardt, *Trends Microbiol.* 16, 107-14 (2008).
J. Wolinska, K. C. King, *Trends Parasitol.* 25, 236-244 (2009).
E. Galiana, S. Fourré, G. Engler, *Environ. Microbiol.* 10, 2164-2171 (2008).
S. Kamoun, *Annu. Rev. Phytopathol.* 44, 41-60 (2006).
C. Darwin, *John Murray, London,* 67 p (1859).
S. J. Gould, *Belknap* (*Harvard University,* 473-474 p (2002).
E. Galiana, S. Fourré, G. Engler, *Environ. Microbiol.* 10, 2164-2171 (2008).
G. Petroni, F. Dini, F. Verni, G. Rosati, *Mol. Phylogenet. Evol.* 22, 118-130 (2002).
S. Ischii, T. Shimoyama, Y. Hotta, K. Watanabe, *BMC Microbiol.* 8, 6 (2008).

The invention claimed is:

1. A method for treating plants for an infection by phytopathogenic oomycetes by contacting plants with the strain of *Phoma* deposited with the Collection Nationale de Cultures de Microorganismes of the Pasteur Institute on Feb. 25, 2010 under the CNCM number I-4278, a culture supernatant of said strain or a combination thereof.

2. The method of claim 1, wherein the culture supernatant is characterized in that it comprises at least one metabolite having a size lower than or equal to a value between 0.18 μm and 0.22 μm.

3. The method of claim 1 wherein the strain or culture supernatant is characterized in that it at least partially inhibits the growth of phytopathogenic oomycetes.

4. The method of claim 1, wherein the oomycetes is of the genus *Phytophthora*.

5. The method of claim 1, wherein the oomycetes is *Phytophthora parasitica*.

6. The method of claim 1, wherein the plants are contacted with the culture supernatant of the strain of *Phoma*.

7. The method of claim 6, wherein the culture supernatant is obtained by:

cultivating the strain of *Phoma* deposited with the Collection Nationale de Cultures de Microorganismes of the Pasteur Institute on Feb. 25, 2010 under the CNCM number I-4278, suspending the culture obtained in water, filtering the suspension through a sieve from 0.18 μm to 0.22 μm, and collecting the filtered solution.

8. The method of claim 7, wherein the suspension is centrifuged between 1500 g and 6000 g for 1 to 10 minutes before filtering the suspension.

9. The method of claim 7, wherein the suspension is centrifuged at 2000 g for 2 minutes before filtering the suspension.

10. The method of claim 1, wherein the plants are tobacco, tomato, potato, sweet pepper, grapevine, sunflower, or fruit trees.

* * * * *